US008271202B1

(12) United States Patent (10) Patent No.: US 8,271,202 B1
Fernandez (45) Date of Patent: Sep. 18, 2012

(54) MODIFIED HOST BIO-DATA MANAGEMENT

(76) Inventor: Dennis S. Fernandez, Atherton, CA (US)

( * ) Notice: Subject to any disclaimer, the term of this patent is extended or adjusted under 35 U.S.C. 154(b) by 1028 days.

(21) Appl. No.: 11/588,529

(22) Filed: Oct. 26, 2006

Related U.S. Application Data

(63) Continuation of application No. 10/074,835, filed on Feb. 11, 2002, now abandoned.

(51) Int. Cl.
*G01N 33/48* (2006.01)
*G01N 31/00* (2006.01)
*G06G 7/48* (2006.01)
*G06G 7/58* (2006.01)

(52) U.S. Cl. ............... 702/19; 702/22; 703/11; 703/12
(58) Field of Classification Search .................. None
See application file for complete search history.

(56) References Cited

U.S. PATENT DOCUMENTS

| | | | |
|---|---|---|---|
| 4,216,462 A * | 8/1980 | McGrath et al. ............. 600/301 |
| 5,041,138 A | 8/1991 | Vacanti et al. |
| 5,558,638 A | 9/1996 | Evers et al. |
| 5,624,840 A | 4/1997 | Naughton et al. |
| 5,759,830 A | 6/1998 | Vacanti et al. |
| 5,785,964 A | 7/1998 | Naughton et al. |
| 5,837,832 A | 11/1998 | Chee et al. |
| 5,874,219 A | 2/1999 | Rava et al. |
| 5,882,930 A | 3/1999 | Baier |
| 5,915,240 A | 6/1999 | Karpf |
| 5,974,389 A | 10/1999 | Clark et al. |
| 5,985,353 A | 11/1999 | Lawton et al. |
| 6,027,744 A | 2/2000 | Vacanti et al. |
| 6,027,935 A | 2/2000 | Purchio et al. |
| 6,153,743 A | 11/2000 | Hubbell et al. |
| 6,168,948 B1 | 1/2001 | Anderson et al. |
| 6,197,595 B1 | 3/2001 | Anderson et al. |
| 6,207,392 B1 | 3/2001 | Weiss et al. |
| 6,245,511 B1 | 6/2001 | Gulati |
| 6,306,610 B1 | 10/2001 | Bawendi et al. |
| 6,326,144 B1 | 12/2001 | Bawendi et al. |

(Continued)

OTHER PUBLICATIONS

Han et al., Quantum-dot-tagged microbeads for multiplexed optical coding of biomolecules, Nature Biotechnology, 2001, 19, 631-635.*

(Continued)

*Primary Examiner* — Larry D Riggs, II
(74) *Attorney, Agent, or Firm* — Fernandez & Associates, LLP

(57) ABSTRACT

Modified host bio-data includes biogenetic modeling, sequence engineering, material manufacturing, gene therapy, embedded sensing, programmable operation, tissue scaffolding, clinical trials, contamination checks, and host monitoring. Bio-data are managed for device malfunction or infectious release. Genetically programmable finite state module having partitions or multi-cavity may be accessed for embedded host biometric application. Electronic computer or functionally equivalent system or distributed systems for processing digital data serves to manage modified host data. Unique host identifier and modification indication are stored or accessed in authenticated manner. Modification may be structural tissue regeneration or genetic therapy. Host condition is monitored by accessing host identifier and modification indication, per sensor signal generated by embedded sensors, accessible by wireless communication, generated per request signal, and generated by silicon or quantum dot devices, each sensor partitioned separately in multi-partition device. Device is programmed to switch states of partitions. Sensor signal may indicate contamination. Sensor set corresponds with state device set of finite state machine, so state device indicates state per first sensor sensing host modification, and other state device indicates other state in response to second sensor sensing modification.

18 Claims, 1 Drawing Sheet

U.S. PATENT DOCUMENTS

| | | | |
|---|---|---|---|
| 6,484,104 | B2 | 11/2002 | Abraham-Fuchs |
| 6,497,729 | B1 | 12/2002 | Moussy et al. |
| 6,666,214 | B2* | 12/2003 | Canham ........................ 128/899 |
| 6,970,741 | B1* | 11/2005 | Whitehurst et al. .............. 607/3 |
| 2002/0022273 | A1 | 2/2002 | Empedocles et al. |
| 2002/0135336 | A1 | 9/2002 | Zhou et al. |
| 2002/0182658 | A1 | 12/2002 | Polak et al. |
| 2003/0044775 | A1 | 3/2003 | Gulati |
| 2003/0056137 | A1 | 3/2003 | Huelskamp |
| 2003/0115325 | A1* | 6/2003 | Cohen et al. .................. 709/225 |

OTHER PUBLICATIONS

Lake et al., Single and multiband modeling of quantum electron transport through layered semiconductor devices, J. Appl. Phys, 1977, 81(12), 7845-7869.*

Jain (DDT 1999, Aug. 4(8), 346-349).*

U.S. Appl. No. 10/074,835, filed Feb. 11, 2002, Dennis Fernandez.

U.S. Appl. No. 10/379,860, filed Mar. 4, 2003, Dennis Fernandez.

U.S. Appl. No. 10/913,999, filed Aug. 6, 2004, Dennis Fernandez.

U.S. Appl. No. 11/188,251, filed Jul. 21, 2005, Dennis Fernandez.

U.S. Appl. No. 11/187,745, filed Jul. 21, 2005, Dennis Fernandez.

Wilkin, Scott D., Sara C. Michelmore, "Diagnostics Companies Should be on Your Requisition List," In Vitro Diagnostic Industry, SG Cowen, Oct. 2001.

"Couple." Merriam-Webster Online Dictionary, [online], [last visited Nov. 29, 2007]. Retrieved from the Internet <URL: http://www.merriam-webster.com>.

"Network." Merriam-Webster Online Dictionary, [online], [last visited Jun. 1, 2007]. Retrieved from the Internet <URL: http://www.mw1.merriam-webster.com/dictionary/network>.

Tierney, et al. "Table 4-3. Treatment choices for cancers responsive to systemic agents." in Tierney L.M., Current Medical Diagnosis (Appleton & Lange, 38th edition, 1999), pp. 79-81.

Kiersey, et al. "Different Drums and Different Drummers." in: Kiersey, D., Please Understand Me: Character & Temperament Types (Prometheus Nemesis Book Company, 5th Edition, 1984), pp. 1-26.

Hudson, Donna L. & Cohen, Maurice E. Neutral Networks and Artificial Intelligence for Biomedical Engineering, Wiley-IEEE Press, 2000. pp. 225-260.

Goslin, Gregory Ray. A Guide to Using Field Programmable Gate Array (FPGAs) for Application-Specific Digital Signal Processing Performance. Xilinx [online]. 1995. Retrieved from the Internet <URL: http://www.xilinx.com/appnotes.dspguide.pdf>.

Ignoffo, et al. "Cancer Chemotherapy Pocket Guide." Lippincott Williams & Wilkins, 1998. pp. 271-373.

Alnylam Pharmaceuticals. An Introduction to RNA Interference (RNAI) and Drug Development. (2003) [online]. alnylam.com. Retrieved from the Internet <URL:http://www.alnylam.com/Files/Media_Kit/aln208_primer_07.pdf> pp. 1-13.

Reuters. Cancer Patients Pray, Use Herbs, But Quietly [online], [Jun. 6, 2004]. Retrieved from the Internet <URL: http://www.cancerpage.com/news/article.asp?id=7151>.

Peiwen, Li. "Management of Cancer with Chinese Medicine." Donica Publishing, 2003. pp. 17-544.

Prediction Tools—A Tool for Doctors & Patients. Memorial Sloan Kettering Cancer Center [online], Dec. 2003 [retrieved on Jan. 13, 2004]. Retrieved from the Internet: <URL:http://www.mskcc.org/mskcc/html/5794.cfm>.

Paoloni, M and D.J. Argyle. RNA Interference: A New Tool for Gene Silencing in Cancer, Document No. P3016.0903 [online], [Jul. 20, 2004]. Retrieved from the Internet <URL:http://www.ivis.org>.

"Apparatus." Merriam-Webster Online, [online], [last visited Dec. 18, 2006]. Retrieved from the Internet <URL: http://www.m-w.com/dictionary/apparatus>.

"Finite State Machine." (Black, Paul E.) May 12, 2008, [online]. Retrieved from the Dictionary of Algorithms and Data Structures using the Internet <URL:http://www.itl.nist.gov/div897/sqg/dads/HTML/finiteStateMachine.html>.

Bassett, et al., "Gene Expression Informatics—It's All in Your Mine," Nature Genetics Supplement, vol. 21 (Jan. 1999), pp. 51-55.

Johnson-Winegar, Anna. Department of Defense Biological Defense Program Needs for Strategic Biotechnology Development. BIO-Defense and Homeland Security Procurement Conference and Expo [online], Apr. 30, 2002. Retrieved from the Internet <URL: http://www.dtic.mil/cgi-bin/GetTRDoc?Ad=ADA423877&Location=U2&doc=GetTRDoc.pdf>.

IFOAM. Position on Genetic Engineering and Genetically Modified Organisms. [online], [May 2002]. Retrieved from the Internet <URL:http://www.ifoam.org/press/positions/pdfs/IFOAM-GE-Position.pdf>. pp. 1-3.

Tomasek, et al. "Myofibroblasts and Mechano-Regulation of Connective Tissue Remodeling," Nature, vol. 3, (May 2002), pp. 349-363.

Williams, D.F. "Biomaterials and tissue engineering in reconstructive surgery," Sadhana, vol. 28, Parts 3&4 (Jun./Aug. 2003), pp. 563-574.

Ledley, Fredd. "Gene Therapy in Pediatric Medicine," Advances in Pediatrics, vol. 43 (Oct. 18, 1996), pp. 1-21.

Petrovsky, Nikolai, et al. Bioinformatics—changing the face of life sciences research. vLifeScience [online], 2002 [retrieved on Feb. 3, 2002]. <URL: www.vlifescience.com.au>.

Garfinkel, Simson L. Biological Computing. MIT's Magazine of Innovation Technology Review [online], [May/Jun. 2000]. Retrieved from the Internet <URL:http://www.technologyreview.com/computing/12087/page1>.

Ideker, et al. "A New Approach to Decoding Life: Systems Biology," Annual Review of Genomics and Human Genetics, vol. 2 (Sep. 2001), pp. 343-372.

Blakeslee, Sandra. "Health Risks at Tissue Banks," San Francisco Chronicle, (Jan. 20, 2002), pp. A9.

Okarma, Thomas B. "Prospects for Cellular Therapies in the Treatment of Chronic Disease," Journal of Commercial Biotechnology, vol. 6 (2000), pp. 300-307.

Johnson, R. Colin. Scientists Activate Neurons with Quantum Dots. EEtimes.com, [online], [Dec. 4, 2001]. Retrieved from the Internet <URL:http://www.eetimes.com/story/OEG20011204S0068>.

Gardner, et al. "Construction of a Genetic Toggle Switch in Escherichia coli," Nature, vol. 403 (Jan. 20, 2000), pp. 339-342.

Tomsho, Robert. "Noninvasive Test for Colon Cancer is Developed," Wall Street Journal, (Jan. 31, 2002), pp. B10.

Murray, Charles J. Injectable Chip Opens Door to Human Barcode. EETimes.com, [online], [Jan. 4, 2002]. Retrieved from the Internet <URL:http://www.eetimes.com/story/OEG20020104S0044>.

Press Release. Verichip, Miniaturized, Implantable Identification Technology with Multiple Medical, Security, and Emergency Applications. Applied Digital Solutions—Verichip Technology [online], Dec. 19, 2001 [retrieved on Dec. 19, 2001]. Retrieved from the Internet: <URL: http://www.adsx.com/Verichip/Verichip.html>.

The Economist. The Good of Small Things. Nanotechnology in biology, Economist.com, [online], [Dec. 20, 2001]. Retrieved from the Internet <URL:http://www.economist.com/science/displaystory.cfm?story_id=E1_JTGSNV>.

Catimel, Bruno, et al. Biosensors & proteomics. VLifeSciences [online], Feb. 2002 [retrieved on Feb. 3, 2002]. Retrieved from the Internet <URL:http://www.vLifeScience.com.au/Article/Display/1,2906,598,00.html>.

Garfinkel, Simson L. Hack License. MIT's Magazine of Innovation Technology Review [online], [Mar. 2005]. Retrieved from the Internet <URL:http://www.technologyreview.com/printer_friendly_article.aspx?id=14254&channel=business&section=>.

* cited by examiner

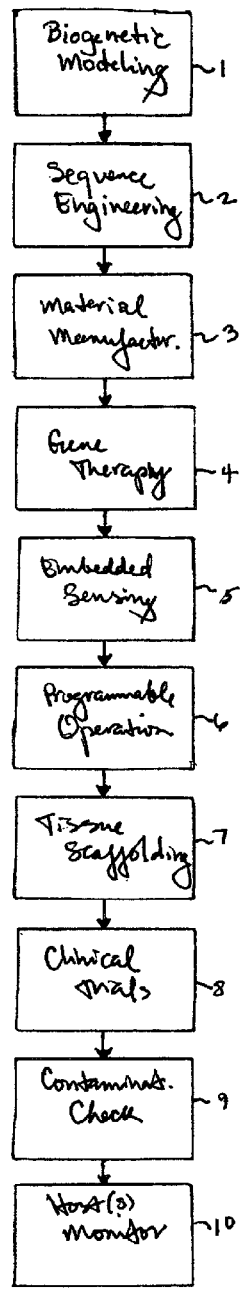
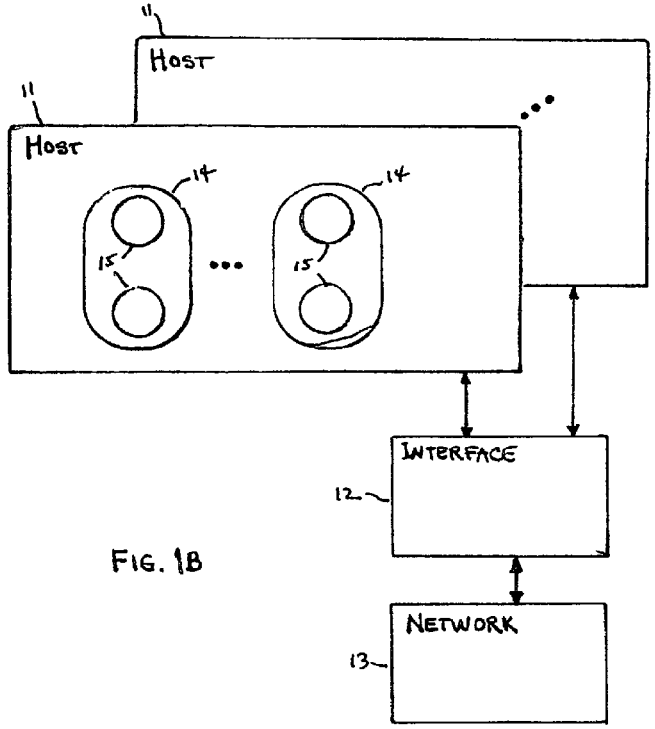
FIG. 1B
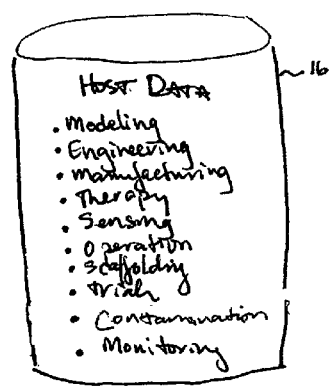
FIG. 1C
FIG. 1A

MODIFIED HOST BIO-DATA MANAGEMENT

CROSS-REFERENCE TO RELATED APPLICATION

This application is a continuation of U.S. parent patent application Ser. No. 10/074,835 filed on Feb. 11, 2002 now abandoned.

FIELD OF INVENTION

Field covers information system for managing bio-data, particularly of modified hosts.

BACKGROUND

For medical, research, cosmetic, or other reasons, biological hosts (i.e., people, animals, plants, etc.) may be modified, for example, structurally, by introducing physical implants or other device within host tissue, or genetically, by introducing genetic material within host cells. Because such modification may have undesirable consequence, such as device malfunction or infectious release, there is need to manage certain bio-data effectively.

SUMMARY

Modified host bio-data comprises biogenetic modeling, sequence engineering, material manufacturing, gene therapy, embedded sensing, programmable operation, tissue scaffolding, clinical trials, contamination checks, or host monitoring; such bio-data being managed for possible device malfunction or infectious release. Optionally, genetically programmable finite state module having partitions or multi-cavity may be accessed for embedded host biometric application.

Electronic computer or functionally equivalent system or network-distributed systems for processing digital data serves to manage modified host data. Unique host identifier and modification indication are stored. Preferably, host identifier is accessed in authenticated manner. In particular, modification may be structural, e.g., host tissue regeneration, and/or genetic, e.g., host gene therapy. Further, host condition may be monitored by accessing host identifier and modification indication.

In addition, modification is indicated by host sensor signal, preferably generated by sensor(s) embedded in the host, accessible by wireless communication, generated responsively to request signal, and/or generated by quantum dot device(s) in contact with host modification, each sensor being partitioned separately in multi-partition device for sensing host modification(s). Multi-partition device may be programmable to switch state(s) associated with partition(s). Moreover, host sensor signal may indicate contamination condition.

Preferably, sensor apparatus monitors host modification(s) in partitions in a multi-partition device. For example, sensor pair corresponds respectively with state device pair, providing finite state machine. Thus, while first state device indicates first state in response to first sensor sensing first host modification, and second state device indicates second state in response to second sensor sensing second host modification. State device(s) may be programmed to indicate programmed state(s). Additionally, sensor(s) may be quantum dot device, and/or silicon device having cavity, as well as being coupled wirelessly by radio transmission to network interface.

BRIEF DESCRIPTION OF FIGURES

The accompanying drawings which are incorporated in and form a part of this specification, illustrate embodiments of the invention and together with the description, serve to explain the principles of the invention:

FIG. 1A flow chart shows representative steps for modified host data management.

FIG. 1B shows generalized diagram of modified host system.

FIG. 1C shows sample modified host data structure.

DETAILED DESCRIPTION

Electronic computer or functionally equivalent system or distributed systems for processing digital data serves to manage modified host data. Unique host identifier and modification indication are stored electronically. Preferably, host identifier is accessed through network in authenticated manner. In particular, host organism modification may be structural, e.g., host tissue regeneration, and/or genetic, e.g., host gene therapy. Further, host condition may be monitored by accessing host identifier and modification indication as digital data.

In addition, modification is indicated by host sensor signal, preferably generated by sensor(s) embedded in or otherwise coupled to host, accessible by wireless communication electronics, generated interactively or responsively to request or query signal, and/or generated by semiconductor-based quantum dot device(s) in contact with host modification material, each sensor being partitioned or otherwise positioned separately in multi-partition device for sensing or otherwise detecting host modification(s). Multi-partition device may be programmable or otherwise reconfigurable to switch state(s) associated with partition(s), per internal host condition change or external electronic instruction or other stimulus. Moreover, host sensor signal may specifically indicate contamination or infection condition associated with host organism.

Preferably, sensor apparatus described herein regularly or occasionally monitors host modification(s) in partition sites in a multi-partition device. For example, sensor pair corresponds respectively with state device pair, thus providing finite state machine. Hence, while first state device indicates first state in response to first sensor sensing first host modification; second state device indicates second state in response to second sensor sensing second host modification. State device(s) may be programmed or otherwise reconfigured to indicate binary or other analog programmed state(s). Additionally, sensor(s) may be implemented using quantum dot device, and/or silicon device having cavity, as well as being coupled wirelessly by radio transmission for communication to network interface.

As described further herein, modified host bio-data may include biogenetic modeling, sequence engineering, material manufacturing, gene therapy, embedded sensing, programmable operation, tissue scaffolding, clinical trials, contamination checks, and/or host monitoring. Such bio-data is managed for possible device malfunction or infectious release. Accordingly, genetically programmable finite state module having partitions or multi-cavity may be accessed electronically for embedded host biometric software or other firmware application.

Reference is made in detail to the preferred embodiments of the invention. While the invention is described in conjunction with the preferred embodiments, the invention is not intended to be limited by these preferred embodiments. On the contrary, the invention is intended to cover alternatives, modifications and equivalents, which may be included within the spirit and scope of the invention as defined by the appended claims.

Furthermore, in the following detailed description of the invention, numerous specific details are set forth in order to provide a thorough understanding of the invention. However, as is obvious to one ordinarily skilled in the art, the invention may be practiced without these specific details. In other instances, well-known methods, procedures, components, and circuits have not been described in detail so that aspects of the invention will not be obscured.

FIG. 1A flow chart shows representative steps for modified host data management. In one data-processing embodiment for implementing one or more aspects of such process steps, it is contemplated that a computer system using one or more processors and storage devices, preferably being accessible by other users or nodes across a local or wide-area digital network, is programmed or otherwise configured functionally to perform operations for managing modified host data.

As understood herein, term "modified host data" refers generally to any information or electronic data registry, record or database generated and/or stored pertaining to one or more identifiable biological host or organism, which uniquely has been modified from a previous same host condition, such as a structural tissue regeneration or genetic therapy treatment. Host identifier may be personally unique, yet secure, authenticated, encrypted, or otherwise restricted to preserve actual host identity and anonymity. Modified host data may comprise text, graphics, images, video, and other document media format, as well as be embodied in flat or hierarchical form, in any standalone or distributed multi-processor or storage computing system(s).

In particular, modified host data 16, shown in FIG. 1C, may describe specifically identified host modification pertaining to biogenetic modeling 1, sequence engineering 2, material manufacturing 3, gene therapy 4, embedded sensing 5, programmable operation 6, tissue scaffolding 7, clinical trials 8, contamination check 9, or host monitor 10.

Hence, in accordance with one or more host modification capability of the integrated data processing embodiment, particularly with respect to activity associated uniquely to certain biological host, such as identified human subject, various related or unrelated step or process may be conducted, including: biogenetic modeling 1 (i.e., bioinformatic analysis or other computer-implemented modeling of one or more host-specific genetic attribute, such as personal gene or sequence information for simulated or possible modification,) sequence engineering 2 (i.e., actual modification of personal gene or sequence using one or more conventional recombinant or genetic engineering technique,) material manufacturing 3 (i.e., actual production operation to manufacture one or more various material including modified personal gene or sequence,) gene therapy 4 (i.e., actual introduction of one or more various material including modified personal gene or sequence in same or other host,) embedded sensing 5 (i.e., actual bio-sensing of one or more modified or unmodified host externally and/or internally,) programmable operation 6 (i.e., actual functional configuration, computing, or switching of one or more digital device in one or more host,) tissue scaffolding 7 (i.e., actual reconstruction, growth, or generation of host tissue or structure,) clinical trials 8 (i.e., any clinical, regulatory, or other compliance procedure associated with one or more host,) contamination check 9 (i.e., any inspection, screening, or other indication of one or more host to determine sourcing, presence or likelihood of one or more contamination or infection,) or host monitor 10 (i.e., any ongoing or incidental inspection, screening or other indication of one or more host to monitor condition.)

Thus, as shown in FIG. 1C, modified host data 16 is implemented preferably in one or more electronic database, memory storage, or other network-accessible, searchable, secure information repository using various relational and/or object-oriented database management software, firmware and/or hardware to store, update, edit, access, retrieve, archive, or otherwise represent one or more host-specific modification attribute. In accordance with attribute-collection aspect of integrated data-management scheme, such host-specific modification attribute is explicitly associated, logically linked, or otherwise deterministically identifiable with a particular host, or set of hosts, having same attribute, thereby accurately recording various host-specific modification, and facilitating host diagnosis by comparing, correlating, contrasting, or otherwise interpreting in integrated process related and unrelated attributes.

For example, modified host data 16 may describe or otherwise refer to one or more host-specific genetic or other functional simulation models or bayesian network for computer-implemented analysis or other bioinformatic or software tool modeling of one or more host-specific genetic attribute, such as personal protein, gene, or other sequence information for simulated or possible engineering or other genetic modification.

Thus, computer-aided analysis of host modification may apply to determine and evaluate uniquely for specific host: gene sequence engineering, material or tissue manufacturing, proper gene therapy procedure, embedded host tissue sensing, programmable sensor operation within host, host tissue scaffolding and generation, proper host clinical trial procedures, host contamination checks, and/or ongoing host monitoring and data recordation, as described herein.

Additionally for uniquely-identified host, modified host data 16 may describe or otherwise refer to one or more host-specific actual history, status, or condition of engineering or other modification of personal protein, gene or sequence using one or more recombinant or genetic engineering technique.

Furthermore for uniquely-identified host, modified host data 16 may describe or otherwise refer to one or more host-specific history, status, or condition of actual production operation to manufacture one or more tissue or other biological material including modified personal protein, gene or sequence.

Also for uniquely-identified host, modified host data 16 may describe or otherwise refer to one or more host-specific history, status, or condition of actual introduction of one or more material including modified personal protein, gene or sequence for therapeutic or other medical procedure or treatment in certain host.

Further for uniquely-identified host, modified host data 16 may describe or otherwise refer to one or more host-specific history, status, or condition of actual bio-sensing of certain host or tissue thereof, either through external and/or internal contact.

In addition for uniquely-identified host, modified host data 16 may describe or otherwise refer to host-specific history, status, or condition of actual functional configuration, computing, or switching of one or more digital programmable or state device in certain host.

Moreover for uniquely-identified host, modified host data 16 may describe or otherwise refer to host-specific history, status, or condition of actual reconstruction, growth, or generation of certain host tissue or structure.

Furthermore for uniquely-identified host, modified host data 16 may describe or otherwise refer to host-specific history, status, or condition, any clinical, regulatory, or other compliance procedure associated with certain host treatment or other medical procedure.

Additionally for uniquely-identified host, modified host data 16 may describe or otherwise refer to host-specific history, status, or condition of any inspection, screening, or other indication of certain host to determine sourcing, presence or likelihood of one or more contamination or infection.

And for uniquely-identified host, modified host data 16 may describe or otherwise refer to host-specific history, status, or condition of any ongoing or incidental inspection, screening or other indication of certain host to monitor condition.

FIG. 1B shows functional diagram of modified multi-host system, optionally coupling general computer, storage, databases, applications software, and other digital network resource 13 via electronic and/or wireless communication interface 12.

For example, via integrated modified-host monitoring approach, one or more host 11 may couple one or more sensor 14 data and/or signals electronically via wired connections or radio frequency transceiver communication to local or wide area network using conventional or standard technique (e.g., Internet Protocol.) Optionally, sensor 14 may be physically embedded, implanted, non-invasively attached, or otherwise installed structurally within such modified host 11 scaffold, or other tissue therein, and communicate through wireless signal transducer to interface 12, possibly placed within host garment. Host scaffold may comprise tissue, such as ligaments, tendons, bones, skin, etc., and/or biomedical device, such as pacemaker, defibrillator, artificial joint, heart valve, medication pump, etc. For example, various implementation of host tissue scaffold is described in U.S. Pat. Nos. 5,041,138, 5,759,8300, and 6,027,744 (Vacanti et al.,) as well as 5,785,964 (Naughton et al.,) which are hereby incorporated by reference.

In addition, sensors 14 may comprise gene-regulatory circuit, optical biosensor, semiconductor nanocrystal, quantum dot device, and/or silicon device having cavity, and operate effectively as functionally or genetically programmable finite state machine modules, using one or more adjacent, partitioned, or bi-stable state or register elements 15, which preferably are configurable digitally to modify, toggle or switch bit, or state, for example, according to external signal or instructions (e.g., from network processor or application) or internally according to measured host condition.

For example of representative sensor design and operation, construction of sample genetic toggle switch is described by T. Gardner et al. in *Nature, vol.* 403, pp. 339-342, Jan. 20, 2000, which is hereby incorporated by reference. As additional example, semiconductor quantum-dot sensor implementation is described by R. Johnson in EE Times, "Scientists activate neurons with quantum dots," Dec. 4, 2001, as well as in U.S. Pat. Nos. 6,326,144 and 6,306,610 (Bawendi et al.,) and 6,207,392, which are hereby incorporated by reference.

Therefore, in integrated embodiment for modified host bio-data management, it is contemplated that computer-assisted modeling using one or more software applications access specific host bio-data, as described herein, for biological or genetic simulation, especially to evaluate, verify, or prototype possible modifications and effects in response to system perturbations. Moreover, in such host-specific development environment, particular gene sequence may be engineered either actually using sequencing equipment and other laboratory recombinant techniques, preferably in accordance with prior modeling parameters.

If appropriate further, host-specific or such modeled and genetically engineered organic tissue or other material may then be manufactured using available production processes to replicate genetic material, for example, in accordance with various drug production technology. And if appropriate for host medical treatment, for example, viral or cellular gene therapy host-specific procedures may be conducted with reference to or functional integration with available other host bio-data described herein.

Optionally if applicable as well, host-specific embedded sensing of host tissue, cell, or other organic material may be conducted with reference to or functional integration with available other host bio-data described herein. To extent host-specific modification includes implantation, attachment, or other use of programmable or configurable device or sensor, such operation may be conducted with reference to available other host bio-data described herein. Similarly to extent host-specific modification includes host tissue scaffolding, generation, or other structural modification, such operation may be conducted with reference to or functional integration with available other host bio-data described herein.

For example, it is contemplated herein that host-specific modification may be combined with host-specific embedded biosensor operation or gene therapy treatment, such that sensor implantation or treatment infusion occurs with, at or near structural tissue scaffolding or other material modification. Another combination may arise wherein such biosensor operation or related finite state machine disposed within modified tissue structure may be caused to operate or otherwise be programmed or configured according to internal or external signal or stimulus.

Hence, since common host organism (or host set) may serve effectively as integrated platform for potential multiple organic or other functional modification (i.e., structural, genetic, etc.) present database system scheme allows unified personal approach to remember, access, control, and otherwise securely manage host-specific information.

Additionally to extent host-specific modification is conducted in context of one or more clinical trial procedure, such procedure may be done with reference to or functional integration with available other host bio-data described herein. In addition to extent host-specific contamination check is conducted, such procedure may be done with reference to or functional integration with available other host bio-data described herein. And when host-specific monitoring steps are conducted, such steps may be done with reference to or functional integration with available other host bio-data described herein.

The foregoing descriptions of specific embodiments of the invention have been presented for purposes of illustration and description. They are not intended to be exhaustive or to limit the invention to the precise forms disclosed. Obviously, many modifications and variations are possible in light of the above teaching. The embodiments were chosen and described in order to explain the principles and the application of the invention, thereby enabling others skilled in the art to utilize the invention in its various embodiments and modifications according to the particular purpose contemplated. The scope of the invention is intended to be defined by the claims appended hereto and their equivalents.

What is claimed is:

1. Integrated sensor platform for multiple modified-host data comprising:

first sensor comprising semiconductor-based nanocrystal for sensing first host to generate first signal;

second sensor comprising semiconductor-based quantum device for sensing second host to generate second signal;

network interface coupled to first and second sensors; and network accessible information repository coupled to said first and second sensors via said network interface;

wherein a functionally integrated platform couples the first and second sensors via the network interface to a network accessible information repository that collects modified-host data that is data associated, logically linked, or otherwise deterministically identifiable with one or more unique modified-host, such modified-host data being identifiable uniquely to such one or more host and comprising biogenetic modeling data, sequence engineering data, material manufacturing data, gene therapy data, embedded sensing data, programmable operation data, tissue scaffolding data, clinical trials data, contamination check data, and host monitor data structure, such modified-host data storage structure being identifiable uniquely to such one or more host.

2. Platform of claim 1 wherein:

the first or second sensor comprises multi-cavity finite-state machine having pair of bi-stable registers;

wherein said finite-state machine provides binary detection state signal to be stored on said network accessible information repository.

3. Platform of claim 1 wherein:

the first or second sensor is implanted in host tissue scaffold.

4. Platform of claim 1 wherein:

the first or second signal is accessed using Bayesian network software or firmware.

5. Platform of claim 1 wherein:

computer-assisted simulation or modeling is performed using the first or second sensor signal data generated in response to biological host system perturbation.

6. Platform of claim 1 wherein:

the first or second host is modified structurally or genetically.

7. Integrated sensing method for multiple host data comprising steps:

sensing by first sensor comprising semiconductor-based nanocrystal coupled to first host to generate first signal; and sensing by second sensor comprising semiconductor-based quantum device coupled to second host to generate second signal;

wherein network interfaces to first and second sensors, communicating signal from said first and second sensor;

storing said first and second signal;

wherein a functionally integrated platform couples the first and second sensors via the network interface to a network accessible information repository that collects modified-host data that is unified data associated, logically linked, or otherwise deterministically identifiable with one or more unique modified-host, such modified-host data being identifiable uniquely to such one or more host and comprising biogenetic modeling data, sequence engineering data, material manufacturing data, gene therapy data, embedded sensing data, programmable operation data, tissue scaffolding data, clinical trials data, contamination check data, and host monitor data structure, such modified-host data storage structure being identifiable uniquely to such one or more host.

8. Method of claim 7 wherein:

the first or second sensor comprises multi-cavity finite-state machine having pair of bi-stable registers;

wherein said finite-state machine provides binary detection state signal to be stored on said network accessible information repository.

9. Method of claim 7 wherein:

the first or second sensor is implanted in host tissue scaffold.

10. Method of claim 7 wherein:

the first or second signal is accessed using Bayesian network software or firmware.

11. Method of claim 7 wherein:

computer-assisted simulation or modeling is performed using the first or second sensor signal data generated in response to biological host system perturbation.

12. Method of claim 7 wherein:

the first or second host is modified structurally or genetically.

13. Computer-aided attribute collection apparatus comprising:

computer-aided means for collecting modified host data structure;

sensing means coupled to collecting means, such sensing means comprising semiconductor-based nanocrystal or quantum device for sensing one or more host to generate modified host data;

wherein a functionally integrated platform couples the sensing means via a network interface to the collecting means comprising a network accessible information repository that collects modified-host data that is data associated, logically linked, or otherwise deterministically identifiable with one or more unique modified-host, such modified-host data being identifiable uniquely to such one or more host and comprising biogenetic modeling data, sequence engineering data, material manufacturing data, gene therapy data, embedded sensing data, programmable operation data, tissue scaffolding data, clinical trials data, contamination check data, and host monitor data structure, such modified-host data storage structure being identifiable uniquely to such one or more host.

14. Apparatus of claim 13 wherein:

said sensing means comprises multi-cavity finite-state machine having one or more bi-stable register;

wherein said finite-state machine provides binary detection state signal to be stored on said network accessible information repository.

15. Apparatus of claim 13 wherein:

said sensing means is implanted in host tissue scaffold.

16. Apparatus of claim 13 wherein:

collected data structure is accessed using Bayesian network software or firmware.

17. Apparatus of claim 13 wherein:

computer-assisted simulation or modeling is performed using the first or second sensor signal data generated in response to biological host system perturbation.

18. Apparatus of claim 13 wherein:

at least one host is modified structurally or genetically.

* * * * *